United States Patent [19]

Rückert et al.

[11] Patent Number: 5,863,556
[45] Date of Patent: Jan. 26, 1999

[54] PREPARATIONS FOR THE EXTERNAL APPLICATION OF ANTISEPTIC AGENTS AND/OR AGENTS PROMOTING THE HEALING OF WOUNDS

[75] Inventors: Dieter Rückert, Tübingen; Herman Gümbel, Rödermark-Waldacker; Wolfgang Fleischer, Ingelheim; Karen Reimer; Horst Winkler, both of Limburg, all of Germany

[73] Assignee: Euro-Celtique, S.A., Luxembourg

[21] Appl. No.: 903,839

[22] Filed: Jul. 31, 1997

Related U.S. Application Data

[63] Continuation of Ser. No. 293,877, Sep. 19, 1994, abandoned.

[30] Foreign Application Priority Data

Aug. 20, 1993 [DE] Germany ............................ 9312509 U

[51] Int. Cl.⁶ ............................ A61K 31/79; A01N 25/26
[52] U.S. Cl. .................. 424/450; 424/78.04; 424/78.07; 424/78.24; 424/405; 424/417
[58] Field of Search ................................ 424/405, 78.04, 424/78.07, 450, 417, 78.24

[56] References Cited

U.S. PATENT DOCUMENTS

| | | | |
|---|---|---|---|
| 2,706,701 | 4/1955 | Beller et al. | 167/70 |
| 4,113,857 | 9/1978 | Shetty | 424/150 |
| 4,675,009 | 6/1987 | Hymer et al. | 604/304 |
| 5,128,139 | 7/1992 | Brown et al. | 424/450 |
| 5,232,692 | 8/1993 | Isenberg et al. | 424/78.04 |
| 5,552,158 | 9/1996 | Evans et al. | 424/450 |

FOREIGN PATENT DOCUMENTS

| | | | |
|---|---|---|---|
| 0509338A1 | 4/1991 | European Pat. Off. | A61K 91/27 |
| 0613685A1 | 3/1993 | European Pat. Off. | A61K 9/127 |
| 9011781 | 10/1990 | WIPO | A61K 43/00 |

OTHER PUBLICATIONS

Database, WPI, Week 9038, Derwent Publications Ltd., London, GB; AN 90–287819 &JP–A–63 126 820 9 (Shiseido KK), 14 Aug. 1990 "Abstract".

Database WPI, Wiik 8827, Derwent Publications Ltd., London, GB; AN 88–188027 & JP–A–63 126 820 9 (Shiseido KK), 30 May 1988 "Abstract".

Liautard, J. et al., *J. Microencapsulations* (1991), vol. 8, pp. 381–389.

Primary Examiner—Thurman K. Page
Assistant Examiner—Kathryne E. Shelborne
Attorney, Agent, or Firm—Davidson, Davidson & Kappel, LLC

[57] ABSTRACT

The present invention relates to liposomal pharmaceutical preparations which include active agents such as antiseptic agents, wound-healing agents, or combinations thereof, useful in the treatment of external wounds. The active agents are encapsulated in liposomes, and the liposomes are incorporated in pharmaceutical preparations such as liquids, ointments, gels, lotions, or creams capable of delivering the active agents to external wound sites. The invention further relates to methods of preparation of the liposomes and the pharmaceutical preparations, and to methods of treatment of external wounds and ophthalmic infections.

25 Claims, No Drawings

PREPARATIONS FOR THE EXTERNAL APPLICATION OF ANTISEPTIC AGENTS AND/OR AGENTS PROMOTING THE HEALING OF WOUNDS

This application is a continuation of application Ser. No. 08/293,877 filed Sep. 19, 1994 which application is now abandoned.

BACKGROUND OF THE INVENTION

The invention concerns preparations for the external application of agents with antiseptic and/or wound healing promoting properties. The preparations are specifically applied to wounds, skin, mucous membranes and mucosa-like unkeratinized epithelial tissues of humans and animals.

A plurality of different antibiotic and antiseptic agents are known for the topical treatment of infectious maladies. A decisive disadvantage of antibiotic agents is that the infecting bacteria show primary resistances, and can acquire secondary resistances, against these agents. Further, antibiotics quite often lead to patient sensitivity, especially after prolonged treatment. The use of antiseptics such as povidone iodine, also known as polyvidone iodine or PVP iodine, i.e. the poly(1-vinyl-2-pyrrolidin-2-one)-iodine complex, can inhibit the formation of resistances to antiseptic or antibiotic agents by infecting bacteria. Antiseptic agents are also much more rarely allergenic when used in patients as compared to antibiotics.

In the scientific literature liposomes have quite often been disclosed as drug carriers. A non-exhaustive list comprises the following, more recent publications:

Hoekstra, H. J., Van Baare, J., Dutrieux, R. P.: Evaluation of topical therapy and wound healing. European Burn Association 5th Congress, Brighton, England, 1993

Neuhann, T., Sommer, G.: Erfahrungen mit Jod-Povidon zur Behandlung der Reratokonjunctivitis epidemica. Z. prakt. Augenh. 1 (1980), p. 65;

Pleyer, U., Schmidt, K., Thiel, H. J. (eds.): Liposomes in Ophthalmology and Dermatology. Hippokrates Verlag Stuttgart, 1993;

Prufer, K., Sternberg, B.: Liposomen in der Medizin-Eine aktuelle Bestandsaufnahme. Z. arzt. Fortbildung 88 (1994), pp. 257–256;

Rubas, W., Schreier, H.: Liposomen: Fortschritt in Herstellungs-Technologie und Therapie Pharmazie in unserer Zeit, 6 (1991) pp. 255–270;

Schreier, H., Bouwstra, J.: Liposomes as topical drug carriers: dermal and transdermal drug delivery. (Submitted); and Shell, J. W.: Ophthalmic drug delivery systems. Surv. Opthalmol. 29 (1984), 117.

Further, the team of Hoekstra et al. in Beverwijk, Netherlands, has reported on animal experiments with silver sulfadiazine, a chemotherapeutic agent, encapsulated in liposomes and applied to experimental wounds. The results appear to show agent enrichment at the wound bottom and reduced silver resorption, compared with customary silver sulfadiazine ointments.

However, although a lot of attention has been paid for quite some time to liposomes as drug carriers, there appears to be no prior art relating to liposomes as carriers of antiseptic or wound healing promoting agents for external applications.

OBJECTS AND SUMMARY OF THE INVENTION

An object of the instant invention is to provide a well-tolerated, easily applicable antiseptic or wound healing promoting preparation, which provides protracted release and protracted topical effect of the active agent.

A further object of the present invention is to provide a method of producing a pharmaceutically acceptable liposome preparation including an active agent (e.g. an antiseptic agent or a wound-healing agent).

Another object of the present invention is related to the treatment of eye infections using a liposomal pharmaceutical preparation containing an antiseptic agent.

It is a further object of the present invention to provide a method of treating external wounds using a liposomal pharmaceutical formulation which formulation includes an antiseptic agent, a wound-healing promoting agent, or a combination thereof as active ingredients.

According to the invention the technical objects are attained in that the preparation comprises at least one antiseptic and/or wound healing promoting agent in the form of a liposome preparation.

In accordance with the above-stated objectives and others, the present invention is directed in part to a pharmaceutical preparation for external application which preparation contains an antiseptic agent, a wound-healing agent, or a combination thereof, encapsulated in a plurality of liposomes.

An important aspect of the invention is related to the surprising fact that liposomes are highly suited as carriers for antiseptic agents, especially for povidone iodine, and for agents promoting the healing of wounds.

In certain preferred embodiments, a portion of the antiseptic agent or wound-healing agent or combination thereof is not encapsulated in the liposomes.

In certain preferred embodiments, the antiseptic agent may be selected from mercury compounds, phenol derivatives such as thymol, eugenol and hexachlorophene, detergents, iodine and iodine complexes, or mixtures of the foregoing. A particularly preferred embodiment contains povidone iodine as the antiseptic agent.

The wound-healing agent promotes healing of injured tissue. In certain embodiments of the invention, the wound-healing agent is selected from the group consisting of allantoin, an azulene compound, a compound from the vitamin B series, or combinations thereof.

A preferred embodiment of the invention contains at least one antiseptic agent and at least one wound-healing agent.

Liposome size is also an important aspect of the invention. Preferably, the liposomes in the pharmaceutical preparation are in the range from about 20 to about 20,000 nm, more preferably from about 50 to about 4,000 nm, even more preferably from about 500 to about 2,500 nm, and most preferably the liposomes are of a uniform diameter of about 1,000 nm.

The pharmaceutical preparation according to the invention will preferably release the antiseptic agent or wound-healing agent or combination thereof over an extended time period, more preferably over an extended time period of several hours duration (e.g., about 2 to about 12 hours). A particularly preferred embodiment releases the antiseptic agent or wound-healing agent at the same release rate over the extended time period.

A preferred pharmaceutical preparation according to the present invention preferably includes at least one anesthetically active agent.

The pharmaceutical preparation may also include additional conserving or preservative agents, and consistency forming additives that are currently known to one of ordinary skill in the pharmaceutical art.

The pharmaceutical preparation of the present invention may take a variety of different forms according to the vehicle used. In a preferred embodiment, the vehicle is a liquid and the preparation is in the form of a solution or a dispersion comprising liposomes. A particularly preferred embodiment where the pharmaceutical preparation is in the form of a liquid pharmaceutical drop preparation.

In yet another embodiment the vehicle is in the form of a cream base and the resultant pharmaceutical preparation is in the form of a cream. Other embodiments of the present invention include the pharmaceutical preparation in the form of an oil in water or water in oil lotion, an ointment, or a gel (preferably a hydrogel base).

Another preferred embodiment of the invention is a pharmaceutical preparation in the form of a pharmaceutical eyedrop formulation prepared with liposomes encapsulating an antiseptic agent (e.g., PVP iodine solution), and wherein said liposomes are of substantially uniform size. The formulation may additionally comprise customary additives, adjuvants and auxiliary substances of a pharmaceutical eyedrop formulation.

The present invention is further directed towards a method of preparing a liposomal pharmaceutical formulation comprising the steps of dissolving a liposome forming agent in a solvent in a suitable container; evaporating the solvent to form a lipid film on the surface of the container; adding a quantity of PVP iodine solution to said container with the lipid film therein to form a mixture; agitating said mixture to produce liposomes; separating the liposomes and dispersing the liposomes in a sodium chloride buffer solution; and freeze-drying the resultant dispersion. Additionally, the method described may include the further step of filtering the dispersion through a high pressure filtering means subsequent to liposome formation.

The invention also relates to a method of treating external wounds comprising the steps of applying a pharmaceutical preparation to an external wound, wherein the pharmaceutical preparation comprises an antiseptic agent, a wound-healing agent, or a combination thereof, encapsulated in a plurality of liposomes, and a pharmaceutically acceptable vehicle.

Additionally, the invention relates to a method of treating eye infections comprising the steps of applying a dose of a pharmaceutical preparation to the eye of a mammal having an eye infection, wherein the pharmaceutical preparation comprises an antiseptic agent, a wound-healing agent, or a combination thereof, encapsulated in a plurality of liposomes, and a pharmaceutically acceptable vehicle. In a preferred embodiment, the pharmaceutical preparation is in the form of a pharmaceutical eyedrop formulation.

Further advantageous embodiments of the invention will become apparent from the following paragraphs.

DETAILED DESCRIPTION OF THE INVENTION

The liposome preparations according to this invention permit protracted release of the agent or agents, and provide an extended and topical activity at the desired locus of action by interaction with cell surfaces.

Experiments and research carried out by the instant inventors appear to show that, even more unexpectedly, the preparations according to this invention do not only contain the active agent (e.g. povidone iodine) encapsulated in liposomes; there is also some amount of active agent (e.g. antiseptic agent, wound-healing agent) which is not contained inside the liposomes.

The preparations according to the present invention often show a marked initial effect which is observed in addition to the slower, protracted release of the active agent from the liposomes. Without wishing to be bound to any theoretical explanation, it is presently assumed that in addition to active agent encapsulated inside the liposomes, some active agent is present outside of the liposomes, and probably loosely bound to the outer surfaces of the liposomes. This could be due to association of active agent molecules with the liposomal membrane, or it could be due to active agent molecules forming a layer on the liposomal surface, which layer partly or even fully coats the liposome externally. The type and amount of this initial agent effect can, for example, be influenced by varying the concentration of the active agent.

Liposome preparations according to this invention thus make it possible to achieve effects which cannot be provided by customary preparations such as solutions, ointments etc.

The active agent used in the preparations of the present invention may be selected from well-known agents which are classified, e.g., as antiseptic agents, wound-healing agents, and the like. Preferred antiseptic agents comprise the well-known pharmaceutical substances providing fast effect, a broad range of activity, low systemic toxicity and good tissue compatibility. They can e.g. be selected from the group comprising metal compounds, phenolic compounds, detergents, iodine and iodine complexes. A specifically preferred antiseptic agent is povidone iodine.

Preferred wound-healing agents comprise substances which have been described in the literature for such application. Preferred wound-healing agents include substances known to promote epithelization. These include vitamins, specifically from the vitamin B group, allantoin, azulenes, and mixtures thereof, and other agents well known in the art having similar properties.

In preferred embodiments, the liposome preparations containing antiseptic and/or wound-healing agents can comprise further agents such as anaesthetic agents. Inventive preparations can also contain customary further agents, including adjuvants and additives, conserving agents or consistency forming agents such as viscosity adjusting additives, emulgators etc.

The amphophilic substances generally known in prior art to form liposome membranes can be employed in the context of the invention as long as they are pharmaceutically acceptable for the intended application. Presently, liposome forming systems comprising lecithin are preferred. Such systems can comprise hydrogenated soy bean lecithin besides cholesterol and disodium succinate-hexa-hydrate. It is presently specifically preferred to use hydrogenated soy bean lecithin as the sole membrane forming agent.

The known prior art methods for forming liposome structures can generally be used in the context of the invention. Broadly, these methods comprise mechanical agitation of a suitable mixture containing the membrane forming substance and water or an aqueous solution. Filtration through suitable membranes is preferred in forming a substantially uniform liposome size.

The size of the liposomes can vary over generally from about 20 to about 20,000 nm. Liposomes with diameters form about 50 to about 4,000 nm are preferred and liposomes of approximately 1,000 nm diameter are presently most preferred.

One presently preferred field of application is in ophthalmology, e.g., in the treatment of bacterial and viral keratoconjunctivitis, and the pre-operative antiseptic prophylaxis.

A presently highly preferred use of the inventive liposome preparations is in the local treatment of infections of the frontal part of the eye, especially when the liposome preparations contain povidone iodine. Also in this indication, the inventive antiseptic preparations, especially those containing PVP iodine, have the great advantage of not causing resistances and lead to much less allergic reactions, while permitting a very cost-efficient therapy with a broad spectrum of effect. A povidone iodine liposome preparation according to this invention is e.g. effective against adenovirus, the most frequent cause of viral conjunctivitis. This effect is not provided by antibiotic agents.

A pharmaceutical preparation incorporating the liposomes of the present invention can provide extended release of an agent (e.g., an antiseptic agent; wound-healing agent) in an environment of use over an extended period of time. Such a time period may be, for example, of several hours duration. More preferably, the time period is in the range of about 4 to about 30 hours duration, and most preferably, from about 12 to about 24 hours duration.

Further, a liposome preparation of antiseptic agent or a microbicidal agent such as povidone iodine provides protracted release of the agent, e.g., from liposomes located in the frontal part of the eye. This leads to extended effect of the antimicrobial substance, and thus less frequent application, as compared with the customary antiseptic eyedrop preparations.

Preparations according to this invention forms, including solutions, dispersions, lotions, ointments and gels.

Generally, the amount of active agents in an inventive preparation will be determined by the desired effect on the one hand and the carrying capacity of the liposome preparation for the agent on the other hand.

Broadly, a solution or dispersion of active agent in an inventive liposome preparation can range between the lower limit of effectiveness of the agent and the solubility or dispersability limit of the agent in the respective solvent or dispersant.

Similar considerations broadly limit the amount of agent in liquids, lotions, creams, ointments or gels, or other such preparation capable of furthering the usefulness of the invention.

More specifically, for an antiseptic such as povidone iodine, a solution or dispersion in an inventive liposome preparation can contain from about 0.1 to about 10 g of agent in approximately 100 g of preparation. Such a preparation will then typically contain from about 1 to about 5 g of liposome membrane forming substance especially lecithin per 100 g of preparation.

In a lotion, which can be a hydrophilic, amphophilic or a lipophilic lotion, a typical range of active agent will be from about 0.5 to about 10 g agent, and from about 3 to about 8 g, preferably about 5 g of liposome membrane forming agent such as hydrogenated soy bean lecithin, per 100 g of lotion. In the case of a hydrophilic lotion, electrolyte solution will often be used in preparing the liposome containing lotion. A lipophilic lotion will often be made from the agent, a membrane forming substance and lipophilic formation agents such as medium chain length triglycerides etc.

Hydrophilic, lipophilic, or amphophilic creams capable of preparation in accordance with the invention. A hydrophilic cream comprising an inventive liposome preparation will generally comprise between 0.1 and 10 g agent, such as povidone iodine, together with between about 1 and 10 g membrane forming substance and further typical oil in water (O/W) cream forming additives, per 100 g of cream.

A comparable amphophilic cream according to the invention will have similar contents of agent and membrane forming substance such as lecithin, and will have the typical further additives of an amphophilic cream.

A hydrophilic ointment according to the invention can broadly comprise from about 0.1 to about 10 g of active agent and from about 1 to about 10 g liposome membrane forming substance such as lecithin, together with typical prior art ointment basis substances such as Macrogol (TM) and water, in 100 g of ointment.

A non-alcoholic hydrogel according to the invention could broadly comprise from about 1 to about 5 g agent such as povidone iodine, approximately 2 g lecithin and gel forming substances such as Carbopol (TM), with pH-adjusting agent and water to form 100 g of hydrogel.

More specific formulations are notable from the embodiment example.

One preferred method for producing the liposomes of the present invention can generally be described as follows:

The lipid membrane forming components, e.g. lecithin, are dissolved in a suitable solvent such as chloroform or a 2:1 mixture of methanol and chloroform and are filtered under sterile conditions. Then, a lipid film is produced on a sterile high surface substrate, such as glass beads, by controlled evaporation of the solvent. In some cases, it can be quite sufficient to form the film on the inner surface of the vessel used in evaporating the solvent, without using a specific substrate to increase the surface.

An aqueous system is prepared from electrolyte components and the one or more active agents to be incorporated in the liposome preparation. Such an aqueous system can, for example, comprise 10 mmol/l sodium hydrogen phosphate and 0.9% sodium chloride, at pH 7.4; the aqueous system will further comprise at least the desired amount of the active agent, which in the embodiment examples is povidone iodide. Often, the aqueous system will comprise an excess amount of agent or agents.

The liposomes are generally formed by agitating said aqueous system in the presence of said film formed by the lipid components. At this stage, further additives can be added to improve liposome formation; for example, sodium cholate can be added. Liposome formation can also be influenced by mechanical action such as pressure filtration through, for example, polycarbonate membranes, or centrifuging. Generally, the raw liposome dispersion will be washed, for example, with electrolyte solution as used in preparing the above-described solution of the active agent.

When liposomes with the required size distribution have been obtained and washed, they can be redispersed in an electrolyte solution as already described, often also comprising sugars such as saccharose or a suitable sugar substitute. The dispersion can be freeze-dried, and it can be lyophilized. It can, prior to use, be reconstituted by addition of water and suitable mechanical agitation at the transition temperature of the lipid component, which for hydrogenated soy bean lecithin is e.g. about 55° C.

In the following Examples, hydrogenated soy bean lecithin (EPISURON (TM) 200 SH obtainable from Lukas Meyer, Germany or PHOSPOLIPON (TM) 90H obtainable from Nattermann Phospholipid GmbH, Germany) was used. However, other pharmaceutically acceptable liposome membrane forming substances can be used instead, and the person skilled in the art will find it easy to select suitable alternative liposome forming systems from what is described in prior art.

DETAILED DESCRIPTIONS OF THE PREFERRED EMBODIMENTS

The features and advantages of this invention will become notable in more detail from the ensuing description of preferred embodiments. In these embodiments, which include a best mode, povidone iodine is exemplified as an antiseptic agent. This should not, however, be construed as a restriction of this invention to antiseptic agents or, among antiseptic agents, to povidone iodine, although such preparations are specifically preferred.

EXAMPLE 1

In a 1000 ml glass flask, provided with glass beads for increased surface, 51.9 mg cholesterol and 213 mg hydrogenated soy bean lecithin were dissolved in a sufficient amount of a mixture of methanol and chloroform in a 2:1 ratio. The solvent was then evaporated under a vacuum until a film was formed on the inner surface of the flask and on the glass beads.

2.4 g PVP iodine (containing about 10% available iodine) were separately dissolved in 12 ml water.

Again in a separate vessel, 8.77 g sodium chloride and 1.78 g Na2HPOH.2H20 were dissolved in 400 ml water. Further water was added up to a total volume of 980 ml, and then, approximately 12 ml 1N hydrochloric acid were added to adjust pH to 7.4. This solution was then topped up with water to produce exactly 1000 ml.

In a fourth vessel, 900 mg saccharose and 57 mg disodium succinate were dissolved in 12 ml water.

The PVP iodine solution was then added to the lipid film in the flask and the mixture was shaken until the film dissolved. This produced liposome formation from the hydrated lipids in the flask. The product was centrifuged and the supernatant liquid was discarded. The a sufficient quantity of saccharose solution was added to produce 12 ml of solution and the product was again centrifuged. Afterwards the supernatant liquid was again discarded. At this stage, a further washing step, using the sodium chloride buffer solution could be used.

After the last centrifugation step and discarding of the supernatant, a sufficient quantity of sodium chloride buffer solution was added to produce 12 ml of solution, and the liposomes were homogeneously distributed therein. The product was then distributed into vials each containing 2 ml liposome dispersion, and the vials were then subjected to a freeze-drying step.

After the freeze-drying, each vial comprised about 40 mg solids.

The method of Embodiment Example I has a minor disadvantage in that the PVP iodine solution used, due to the high percentage of solids, is rather viscous and thus more difficult to handle.

EXAMPLE II

In a 2000 ml flask provided with glass beads to increase surface, 173 mg hydrogenated soy bean lecithin and 90 mg disodium succinate were dissolved in approximately 60 ml of a methanol/chloroform mix in a 2:1 ratio. The solvent was removed under vacuum until a film was formed.

4 g PVP iodine (10% available iodine) were dissolved in 40 ml of the sodium chloride buffer solution described in Embodiment Example I, and were added to the lipid film in the flask. The flask was then shaken until the film dissolved and liposomes were formed.

The product was centrifuged and the supernatant liquid was discarded.

To the thus produced liposome pellet, further sodium chloride buffer solution was added to produce 40 ml of solution, and the centrifuging step was repeated. The supernatant was again discarded. At this stage, this washing step could be repeated where necessary.

After the final centrifuging and decanting step, sodium chloride buffer solution was again added to the precipitated liposomes to produce 40 ml of homogeneous dispersion. The homogenous dispersion was then distributed into vials, each vial containing about 2 ml liposome dispersion, and the vials were then subjected to a freeze-drying step. This produced approximately 200 mg freeze-dried solids per vial.

From the freeze-dried solids of Examples I and II, further preparations were made as described in subsequent embodiment Examples and Test Reports.

Like that of Embodiment Example I, the above-described method uses a hydrating step after film formation in the presence of organic solvents and aims at inclusion rates of from about 5 to about 15%. These methods generally produce rather large and often multilamellar liposomes.

The above-described methods can be modified by a high pressure filtering step through a suitable membrane such as a polycarbonate membrane after the raw liposomes have been formed or after any of the subsequent washing steps or directly by using high pressure homogenization. This produces much smaller, unilamellar liposomes at increased amounts of encapsulated agent.

Instead of high pressure homogenization, other prior art methods known to provide small uniform sized liposomes can be employed.

EXAMPLE III

A hydrophilic (0/W) cream was prepared from 10 g hydrogenated soy bean lecithin/PVP iodine liposomes as described in Embodiment Example II; these were mixed with 4 g Polysorbate 40 (TM), 8 g cetylstearyl alcohol, 8 g glycerol, 24 g white vaseline, and water to produce 100 g of hydrophilic cream.

EXAMPLE IV

An amphophilic cream was prepared from 10 g hydrogenated soy bean lecithin/povidone iodine liposomes as described in Embodiment Example II; 7.5 g medium chain length triglyceride, 7 g polyoxyethyleneglycerol monostearate, 6 g cetylstearyl alcohol, 8 g propylene glycol, 25 g white vaseline, and water ad 100 g.

EXAMPLE V

A hydrophilic ointment which can be rinsed off with water was prepared using 10 g of liposomal PVP iodine as described in Embodiment Example II, 55 g Macrogol 400 (TM), 25 g Macrogol 4000 (TM), and water ad 100 g.

EXAMPLE VI

A hydrogel was prepared from 4 g liposomal PVP iodine as described in Embodiment Example II, 0.5 g Carbopol 980 NF (TM), sodium hydroxide ad pH 7, water ad 100 g.

Further modifications of the above-described embodiments are envisaged.

Thus, the creams of Embodiment Examples III and IV can have an additional content of an agent known to promote the healing of wounds, such as allantoin. Such an agent will be added in a pharmaceutically useful concentration, in the case of allantoin in the range of 0.1 to 0.5 g, per 100 g of cream. The wound healing agent can be incorporated in the cream base, in which case it will largely be outside the liposomes.

It can, however, be partly or mostly incorporated in the liposomes, in which case it will be added at a corresponding suitable stage of the liposome preparation method.

Similar alternatives are easily envisaged on the basis of the further Embodiment Examples.

It is also possible to prepare embodiments similar to the above-described ones, which comprise an agent capable of promoting the healing of wounds instead of, and not in addition to, the antiseptic agent as e.g. povidone iodine disclosed in the above Embodiment Examples. Presently, it is however preferred to use a wound healing promoting agent (if at all) in addition to an antiseptic agent.

For application of the inventive preparations to a patient, known systems can be used, such as pneumatic pump applicators, two-chamber gas pressure packs etc.

In a pneumatic pump applicator, a bellows device is provided between an upstream and a downstream valve, both valves operating one way in the same direction. A supply of pharmaceutical preparation, such as an ointment or gel, is contained in a reservoir upstream of the valves- and -bellows device.

When compressing the bellows, the downstream valve opens and permits a dosed amount of preparation to leave the device for application. When the bellows is extended, this valve shuts and prevents reentry of the preparation. At the same time, the upstream valve opens and permits preparation from the reservoir to enter into the bellows, for release through the downstream valve upon the next compression step of the bellows.

The reservoir is sealed by a closure element which can move through the reservoir like a piston moves in a cylinder. By the stepwise emptying of the reservoir, this closure element is sucked into the reservoir, so that the remaining amount of pharmaceutical preparation in the reservoir is always sealed off, while at the same time the reservoir can be emptied.

Such a device is useful for pasty preparations, creams, ointments etc.

In a two-chamber gas pressure pack, the pharmaceutical preparation is contained in a bag of flexible plastics film material. Often, this is high pressure polyethylene.

The bag is contained inside a gas tight pressure vessel which further contains a supply of pressurizing gas, very often a compressed inert gas like nitrogen.

The plastic film bag has only one outlet, which is gas-tightly connected to the interior wall of the pressure vessel, surrounding a single opening thereof. The pressurized gas in the vessel tends to compress the bag, driving the pharmaceutical preparation inside the bag out through the opening of the bag and thus through the opening of the vessel. A valve and, in case, spray-head device is provided in the vessel mouth. Operating the valve releases a spray mist, a jet of liquid or a portion of flowable solid such as cream. Using such a system, solutions, emulsions, creams, ointments and gels, dosed and applied.

Dosing inventive preparations efficiency and acceptability tests were then carried out, as follows:

Test I

This was an in-vitro-test of the bactericidal effect provided by an inventive povidone iodine liposome preparation. The test was based on the quantitative suspension test as described in "Richtlinien der Deutschen Gesellschaft fur hygiene und Mikrobiologie", 1989. In this test, the bactericidal agent is used to kill staphylococcus aureus (ATCC 29213), a major problem in hospital hygiene.

The liposome preparation used was that of Embodiment Example I. At different contact times between 1 and 120 minutes, the minimum concentration of the preparation in water was determined which was capable of killing the staphylococci.

The results are shown in Table 1.

TABLE I

| Contact Time (Minutes) | Bactericidal Concentration |
|---|---|
| 1, 2, 3, 4 | ≧0.060% |
| 5, 30, 60 120 | ≧0.015% |
| 120 | ≧0.007% |

The results show that at short contact times (between 1 and 4 minutes) the bactericidal concentration is as low as 0.06% and that at long contact times (120 minutes) the bactericidal concentration can be as low as 0.007%.

Test II

The second test was a placebo-controlled clinical study of the local acceptability (at the eye) of an inventive povidone iodine liposome preparation. An eyedrop formulation was made using the liposomes of Embodiment Example II. It was tried on 15 male test persons. The inventive preparation was always used on one eye of the test person, with physiological sodium chloride solution added as a comparison to the respective other eye.

Specifically, each test person received one drop of PVP iodine liposome preparation in the right eye and one drop of physiological sodium chloride solution in the left eye, and this was twice repeated at hourly intervals. After 5, 30, 65, 95, 125 and 150 minutes as well as after 24 hours after the first application, symptoms were determined. These symptoms included hyperaemia, as measured with a slit/lamp microscope; burning; itching, and tear flow. Each symptom was measured according to a 4 point score with 0 corresponding to no symptom, 1 corresponding to a low degree, 2 corresponding to a medium degree and 3 corresponding to a strong degree of symptom appearance.

A sum score was calculated from the degree scores of all four symptoms and the 7 determination time points. The sum score could thus vary between 0 (=0 times 0 times 0) and 84 (=4 times 3 times 7).

The test persons were between 21 and 36 years old, with an average of 30 years of age. All test persons were healthy and not under medication during the test. Specifically, any illnesses of the eye and of the thyroid were excluded.

One test person was not evaluated for sum score since one control of symptoms after 150 minutes was missed.

The results are notable from Table II.

Overall, the sum score on both eyes was extremely low. It is surprising that on average, the sum score for the eyes treated with the povidone iodine liposome preparation was even lower than that for the eyes receiving physiological sodium chloride solution.

TABLE II

| Sum score | PVP-I-Liposomes | Phys. NaCl-Solution |
|---|---|---|
| | Number of test persons | |
| 0 | 11 | 6 |
| 1 | 3 | 6 |
| 2 | 0 | 2 |
| 3–84 | 0 | 0 |
| Average | 0.21 | 0.71 |
| Standard Deviation | 0.43 | 0.73 |
| Median | 0 | 1 |
| p-Value | 0.02 | |

Eleven test persons treated with the invention's povidone iodine liposome preparation showed no symptoms whatsoever. Three test persons had slight hyperaemia, one felt some very slight burning (this is the above-mentioned test person who could not be evaluated for sum score). On the contrary, only six test persons exhibited no symptoms after receiving physiological sodium chloride solution. Four test persons experienced burning, one of them at two subsequent time points. One test person experienced slight burning and itching of the left eye. A total of four test persons showed some hyperaemia.

The examples provided are not meant to be exclusive. Many other variations of the present invention will be obvious to those skilled in the art, and are contemplated to be within the scope of the appended claims.

What is claimed is:

1. A pharmaceutical preparation for external application comprising
    a compound selected from the group consisting of povidone iodine, a wound healing agent selected from the group consisting of vitamins, an allantoin, or an azulene;
or a combination thereof,
    wherein said compound is encapsulated in a plurality of liposomes.

2. A pharmaceutical preparation according to claim 1, further comprising a pharmaceutically acceptable vehicle, wherein a portion of said povidone-iodine or said wound-healing agent, or said combination thereof contained in the preparation is not encapsulated in said liposomes.

3. A pharmaceutical preparation according to claim 2, wherein at least the greatest part of said povidone-iodine or said wound healing promoting agent, or said combination thereof, is encapsulated inside the liposomes.

4. A pharmaceutical preparation according to claim 1 wherein said wound-healing agent is a compound from the vitamin B series, and combinations of the foregoing.

5. A pharmaceutical preparation according to claim 1 wherein the preparation contains povidone-iodine and at least one wound healing promoting agent.

6. A pharmaceutical preparation according to claim 1 wherein said liposomes are of a substantially uniform size in the range from about 20 to about 20,000 nm.

7. A pharmaceutical preparation according to claim 6 wherein said liposomes are of a substantially uniform size in the range from about 50 to about 4,000 nm.

8. A pharmaceutical preparation according to claim 6 wherein said liposomes are of a substantially uniform size in the range from about 500 to about 2,500 nm.

9. A pharmaceutical preparation according to claim 6 wherein said liposomes are of a substantially uniform size of about 1,000 nm diameter.

10. A pharmaceutical preparation according to claim 2 wherein the preparation releases povidone-iodine, said wound-healing agent, or combination thereof, in an environment of use over an extended time period.

11. A pharmaceutical preparation according to claim 10 wherein said extended time period comprises several hours duration.

12. A pharmaceutical preparation according to claim 10 wherein the preparation releases said povidone-iodine, said wound-healing agent, or combination thereof, at approximately the same release rate over the release time period.

13. A pharmaceutical preparation according to claim 2 further comprising at least one anesthetically active agent.

14. A pharmaceutical preparation according to claim 2 further comprising conserving agents and consistency forming additives.

15. A pharmaceutical preparation according to claim 2, wherein said vehicle is a liquid and said preparation is in the form of a solution or dispersion comprising liposomes.

16. A pharmaceutical preparation according to claim 15, wherein said preparation is in the form of a pharmaceutical drop preparation.

17. A pharmaceutical preparation according to claim 2, wherein said vehicle comprises a hydrophilic, lipophilic, or amphophilic cream base and said preparation is in the form of a cream.

18. A pharmaceutical preparation according to claim 2, in the form of a pharmaceutical oil in water or a water in oil lotion.

19. A pharmaceutical preparation according to claim 2, wherein said vehicle is an ointment base and the preparation is in the form of a pharmaceutical ointment.

20. A pharmaceutical preparation according to claim 2, wherein said vehicle is a gel base and the preparation is in the form of a pharmaceutical gel.

21. A pharmaceutical preparation according to claim 20, wherein said vehicle is a nonalcoholic hydrogel base.

22. A pharmaceutical preparation according to claim 2, wherein the pharmaceutical preparation is in the form of a pharmaceutical eyedrop formulation;
    wherein said liposomes comprise a pharmaceutically acceptable liposome membrane forming substance;
    wherein said povidone-iodine is a 0.1 to 2% PVP iodine solution at least most of which is encapsulated within said liposomes; and
    wherein said liposomes are of substantially uniform size between about 50 and about 4,000 nm, and said formulation may additionally comprise customary additives, adjuvants and auxiliary substances of a pharmaceutical eyedrop formulation.

23. A pharmaceutical preparation according to claim 22 wherein said liposomes are of substantially uniform size, with diameters of about 1,000 nm.

24. The pharmaceutical preparation according to claim 1 wherein said povidone iodine is present in an amount ranging from about 0.1 to about 10 grams per 100 gram of pharmaceutical preparation.

25. The pharmaceutical preparation according to claim 1 wherein said pharmaceutical preparation is in a form selected from the group consisting of lotion, a cream, a hydrophilic ointment and a non-alcoholic hydrogel.

* * * * *

UNITED STATES PATENT AND TRADEMARK OFFICE
CERTIFICATE OF CORRECTION

PATENT NO.    : 5,863,556
DATED         : January 26, 1999
INVENTOR(S)   : Ruckert et al.

It is certified that error appears in the above-identified patent and that said Letters Patent is hereby corrected as shown below:

<u>Title page,</u>
Item [63], please delete the filing date of "Sep. 19, 1994" and replace with -- Aug. 19, 1994 --

<u>Column 1,</u>
Line 7, please delete the filing date of "Sep. 19, 1994" and replace with -- Aug. 19, 1994 --

Signed and Sealed this

Seventeenth Day of June, 2003

JAMES E. ROGAN
*Director of the United States Patent and Trademark Office*